United States Patent [19]

Theeuwes et al.

[11] 4,116,241

[45] * Sep. 26, 1978

[54] OSMOTIC SYSTEM WITH LAMINATED WALL COMPRISING STRUCTURALLY DIFFERENT SEMIPERMEABLE LAMINA

[75] Inventors: Felix Theeuwes, Los Altos; Atul D. Ayer, Belmont, both of Calif.

[73] Assignee: Alza Corporation, Palo Alto, Calif.

[ * ] Notice: The portion of the term of this patent subsequent to Mar. 29, 1994, has been disclaimed.

[21] Appl. No.: 750,773

[22] Filed: Dec. 15, 1976

Related U.S. Application Data

[63] Continuation of Ser. No. 654,194, Feb. 2, 1976, Pat. No. 4,014,334.

[51] Int. Cl.$^2$ .......................... A61K 9/24; A61K 9/44
[52] U.S. Cl. ..................................... 128/260; 424/15; 424/21
[58] Field of Search ............... 128/260, 268, 272, 130; 424/19, 21, 22, 28; 222/95, 386.5

[56] References Cited

U.S. PATENT DOCUMENTS

| | | | |
|---|---|---|---|
| 3,618,604 | 11/1971 | Ness | 128/260 |
| 3,737,521 | 6/1973 | Born | 424/22 |
| 3,811,444 | 5/1974 | Heller | 128/260 |
| 3,832,458 | 8/1974 | Merrill | 424/19 |
| 3,961,628 | 6/1976 | Arnold | 128/260 |
| 3,995,631 | 12/1976 | Higuchi et al. | 128/260 |
| 3,996,934 | 12/1976 | Zaffaroni | 128/268 |
| 4,008,719 | 2/1977 | Theeuwes et al. | 128/260 |
| 4,014,334 | 3/1977 | Theeuwes et al. | 128/260 |
| 4,014,335 | 3/1977 | Arnold | 128/260 |

Primary Examiner—Robert W. Michell
Assistant Examiner—Jerome D. Stremcha
Attorney, Agent, or Firm—Paul J. Sabatine; Thomas E. Ciotti; Edward L. Mandell

[57] ABSTRACT

An osmotic system for delivering a beneficial agent to an environment of use is disclosed. The system comprises a laminate surrounding a compartment and has a passageway through the laminate for releasing agent from the compartment. The laminate comprises at least two laminae; one consisting of a semipermeable, polymeric material that is permeable to the passage of an external fluid and maintains its physical and chemical integrity in the environment of use, and one consisting of a semipermeable polymeric material that is permeable to the passage of fluid, substantially impermeable to the passage of agent and maintains its physical and chemical integrity in the presence of agent. The compartment comprises an active agent that is either soluble in the external fluid and exhibits an osmotic pressure gradient across the laminate against the fluid, or the agent has limited solubility in the fluid and it is mixed with an osmotically effective compound that is soluble in the fluid and exhibits an osmotic pressure gradient across the laminate against the fluid. In operation, agent is released from the system by fluid being imbibed through the laminate into the compartment at a rate controlled by the permeability of the laminate and the osmotic pressure gradient across the laminate producing a solution containing agent, or a solution of compound containing agent which solution in either operation is released through the passageway at a controlled and continuous rate over a prolonged period of time.

11 Claims, 9 Drawing Figures

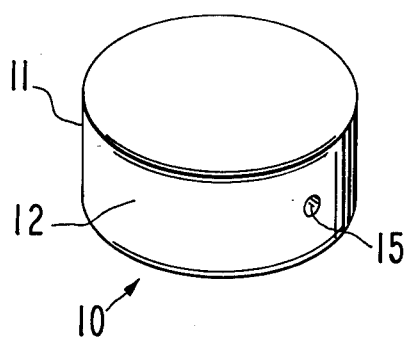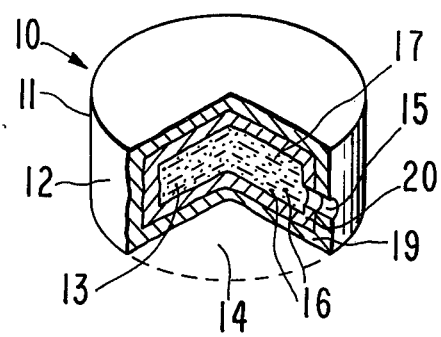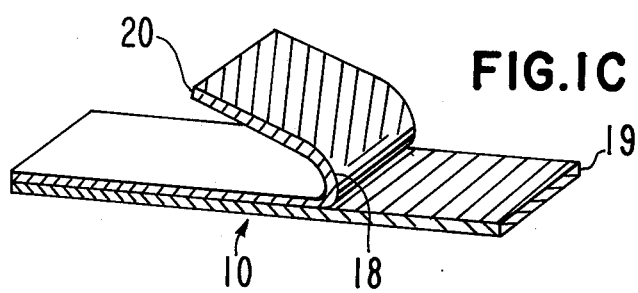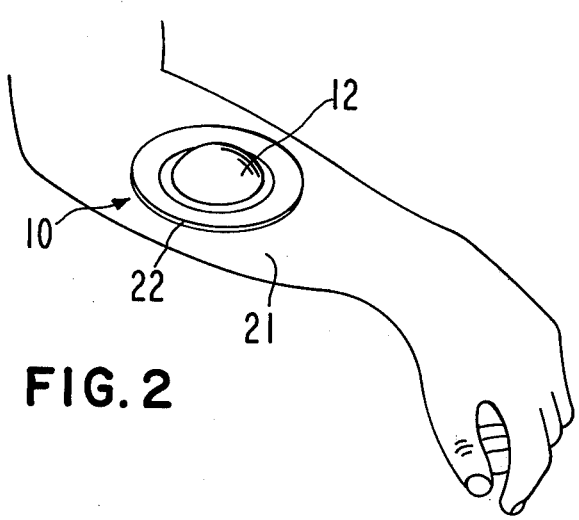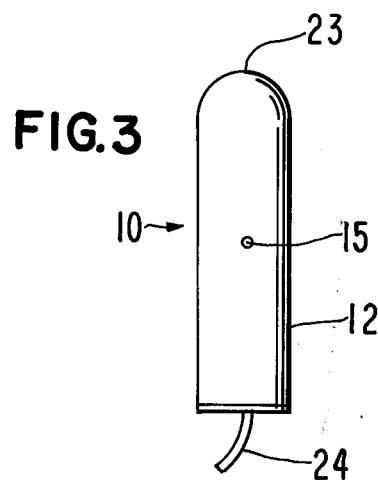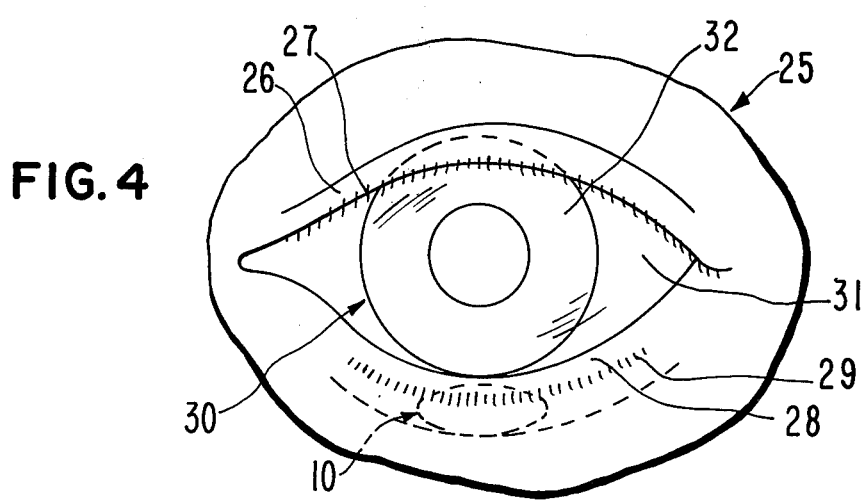

OSMOTIC SYSTEM WITH LAMINATED WALL COMPRISING STRUCTURALLY DIFFERENT SEMIPERMEABLE LAMINA

CROSS-REFERENCE TO RELATED APPLICATION

This application is a continuation of U.S. Pat. App. Ser. No. 654,194, filed on Feb. 2, 1976 and now matured into U.S. Pat. No. 4,014,334. This application and Ser. No. 654,194 are assigned to the ALZA Corporation of Palo Alto, Calif., and benefit of the filing date of Ser. No. 654,194 is claimed herein.

FIELD OF THE INVENTION

This invention pertains to an osmotic system. More particularly, the invention relates to an osmotic system in the form of an osmotic device comprising a semipermeable laminate formed of at least two, non-erodible and inert polymeric semipermeable laminae for delivering an active agent at a controlled and continuous rate over a prolonged period of time to an environment of use.

BACKGROUND OF THE INVENTION

Osmotic systems manufactured in the form of osmotic devices for delivering a beneficial agent to an environment of use are known to the art in U.S. Pat. Nos. 3,845,770 and 3,916,899. The systems in these patents are made with a semipermeable wall that surrounds a compartment containing an agent. The wall is permeable to an external fluid, substantially impermeable to agent, and there is a passageway through the wall for dispensing agent from the system. These systems are extraordinarily effective for delivering an agent that is soluble in the fluid and exhibits an osmotic pressure gradient across the wall against the fluid, and also for delivering an agent that has limited solubility in the fluid and is admixed with an osmotically effective compound that is soluble in the fluid and exhibits an osmotic pressure gradient across the wall against the fluid. These systems release agent by fluid being continuously imbibed through the wall into the compartment at a rate determined by the permeability of the wall and the osmotic pressure gradient across the wall to produce a solution of soluble agent, or a solution of soluble compound containing agent which solution in either operation is dispensed from the system. While the above systems are outstanding and represent a pioneer advancement in the delivery art, and while they are useful for dispensing numerous beneficial agents to an environment of use, there is a rare instance where the environment or the agent may have an unwanted effect on the system that can lead to unwanted results. For example, when the system is placed in an environment that can harm the wall, or the system contains an agent that can harm the wall, in either instance by slowly dissolving or hydrolyzing the wall over a prolonged period of time, these actions can change the system's rate of imbibition that can concomitantly lead to an uncontrolled rate of agent release over a correspondingly prolonged period of time.

OBJECTS OF THE INVENTION

Accordingly, it is an immediate object of this invention to provide an improved osmotic system for the controlled and continuous dispensing of an active agent over a prolonged period of time which system overcomes the problems known to the prior art.

Another object of the invention is to provide an osmotic system that maintains its physical and chemical integrity in both the environment of use and in the presence of agent during the controlled and continuous dispensing of agent over a prolonged period of time.

Yet another object of the invention is to provide an osmotic system designed with a minimum number of parts and having at least one wall formed as a laminate that is substantially non-erodible and inert towards the environment, agents and solutions thereof.

Another object of the invention is to provide an osmotic therapeutic system for dispensing drugs that because of their intrinsic properties, are difficult to dispense, and which drugs can be dispensed with the systems of this invention at a controlled and continuous rate to perform their intended therapeutic effects.

Still a further object of the invention is to provide an osmotic therapeutic system that can administer a complete pharmaceutical regimen to a human for a particular time period, the use of which requires intervention only for initiation and possibly termination of the regimen.

Still a further object of the invention is to provide osmotic systems having a wide spectrum of semipermeable laminates in which properties such as fluid flow-through rate and resistance to chemical and biological attack may be regulated and varied by controlling the laminae forming the laminates.

Yet still another object of the invention is to provide an osmotic system having a laminate that has a high flux rate to fluids, a high degree of exclusion towards agents and improved resistance to hydrolysis and erosion in the enviroment of use and in the presence of agents over a wide pH range.

Yet still another object of the invention is to provide an osmotic system that can deliver all kinds of drugs and has an economic advantage for the user by keeping to a minimum the number of doses to be administered and reduces missed doses because of forgetfulness.

Other objects, features and advantages of the invention will be more apparent to those skilled in the art from the following detailed specification, taken in conjunction with the drawings and the accompanying claims.

SUMMARY OF THE INVENTION

This invention concerns an osmotic system for dispensing an active agent to an environment of use. The system is comprised of a laminate surrounding a compartment and has a passageway through the laminate communicating with the compartment and the exterior of the system. The compartment contains either an agent that is soluble in an external fluid and exhibits an osmotic pressure gradient across the laminate against the fluid, or it contains a mixture of an agent having limited solubility in the fluid and an osmotically effective compound soluble in the fluid that exhibits an osmotic pressure gradient across the laminate against the fluid. The laminate is comprised of at least two semipermeable laminae, each consisting of a different semipermeable, polymeric lamina forming material, with the laminate permeable to fluid, substantially impermeable to agent and compounds, and inert towards agent and the environment of use. Agent is released from the system by fluid being imbibed through the semipermeable laminate into the compartment at a rate controlled by the permeability of the laminate and the osmotic pressure gradient across the laminate producing a solution containing agent that is released through the passageway at a controlled and continuous rate over a prolonged period of time.

BRIEF DESCRIPTION OF THE DRAWINGS

In the drawings, which are not drawn to scale, but are set forth to illustrate various embodiments of the invention, the figures are as follows:

FIG. 1A is a view of an osmotic therapeutic system designed for orally delivering a beneficial agent;

FIG. 1B is a view of the osmotic therapeutic system of FIG. 1A in opened section illustrating the laminate and the compartment of the system;

FIG. 1C is a perpsective view of a portion of the laminate of FIG. 1B with one end peeled open showing the laminae that form the laminate;

FIG. 2 is a view of an osmotic therapeutic system manufactured for topically administering a drug;

FIG. 3 shows an osmotic therapeutic system designed for releasing drug in the vaginal cavity;

FIG. 4 is a front view of the human eye illustrating an osmotic therapeutic system in operative position in an environment of use;

In the drawings and specification, like parts in related figures are identified by like numbers. The terms appearing earlier in the specification and in the description of the drawings, as well as embodiments thereof, are further detailed elsewhere in the disclosure.

DETAILED DESCRIPTION OF THE DRAWINGS

Figure 5:
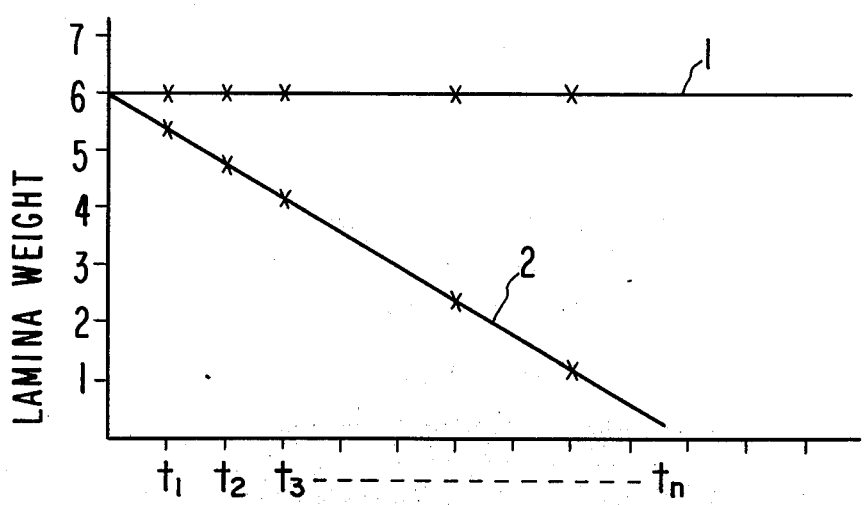
FIG. 5 is a graph comparing a lamina that is inert with a lamina that slowly loses its integrity in the presence of agent.

Turning now to the drawings in detail, which are examples of various osmotic delivery systems of the invention, and which examples are not to be considered as limiting, one example of an osmotic delivery system in the form of an osmotic device is indicated in FIGS. 1A, 1B and 1C considered together by the numeral 10. The phrases "osmotic delivery system" and "osmotic delivery system in the form of an osmotic device" as used for the purpose of the invention are considered as functional equivalents and they also embrace the expressions "osmotic therapeutic system", "osmotic device" and "system".

In FIGS. 1A, 1B and 1C, system 10 is comprised of a body 11 having a laminate 12 that surrounds a compartment 13, seen in FIG. 1B in opened section with a portion of laminate 12 removed at 14, and a passageway 15 in laminate 12 that communicates with compartment 13 and the exterior of system 10. Compartment 13, as seen in FIG. 1B, in one embodiment is a means for containing an agent 16 that is soluble in an external fluid and exhibits an osmotic pressure gradient across laminate 12 against an external fluid, or compartment 13 can contain a mixture of agents 16 with at least one agent exhibiting an osmotic pressure gradient. In another embodiment, compartment 13 contains an agent that has limited solubility or is substantially insoluble in the external fluid is mixed with an osmotically effective compound 17 that is soluble in the external fluid and exhibits an osmotic pressure gradient across laminate 12 against the fluid. Compartment 13 also can contain other compounds such as a surfactant for wetting the agent and a non-toxic dye for either identifying agent 16 or for making release of agent 16 visible to the unaided eye.

Laminate 12, as seen in FIG. 1C, is a section removed from system 10 of FIG. 1B and it is peeled open at 18 for illustrating the structure of laminate 12. Laminate 12 comprises a pair of laminae consisting of an exterior lamina 19 and an inner lamina 20 that are suitably joined in laminar relationship to provide an operative laminate 12 for system 10. Lamina 19 is formed of a unit, semipermeable polymeric lamina forming material that in one embodiment is, (a) permeable to the passage of an external fluid, (b) maintains its physical and chemical integrity in the environment of use, (c) is inert in the environment of use, and (d) provides mechanical support for other laminae forming laminate 12. Lamina 19 is another embodiment is formed of a unit semipermeable polymeric lamina forming material that is, (e) permeable to passage of external fluid, (f) substantially impermeable to compounds present in the environment of use, and has the properties described above in (b), (c) and (d). The phrase "maintains its physical and chemical integrity" as used herein means laminate 12 and laminae 19 and 20 keep their constitution and general preselected shape and design in the environment of use, and in the presence of agent during the active period of agent release even though the system may be flexible and resilient. The terms "inert", "non-erodible" and "resist erosion" mean laminate 12 and laminae 19 and 20 are substantially resistant to physical, chemical, enzymatic and biological attack and reactions in the particular environment of use and in the presence of agent in the compartment. The term "laminate" means the semipermeable laminate surrounding the compartment, and is the functional equivalent of laminated wall and shaped laminated wall.

Lamina 20 is formed of a unit, semipermeable lamina forming material that in one embodiment is, (g) permeable to the passage of an external fluid, (h) substantially impermeable to agent, (i) maintains its physical and chemical integrity in the presence of agent, (j) is inert in the presence of agent, and (k) provides mechanical support for other laminae forming laminate 12. Lamina 20 in another embodiment has the properties described in (g) through (k) and also is, (l) substantially impermeable to compounds present in the environment of use. Also, according to the mode and manner of this invention, laminae 19 and 20 are each formed of a unit or sole semipermeable polymeric lamina forming material that is physically and chemically different with lamina 20 in a presently preferred embodiment more hydrophobic than lamina 19, more inert, having a higher degree of agent and compound rejection, and having a decrease permeability to the passage of an external fluid. While laminae 19 and 20 in a presently preferred embodiment were described with lamina 19 positioned distant from compartment 13 with lamina 20 facing compartment 13, it is understood for other embodiments, lamina 20 can be distant from compartment 13 and lamina 19 can face compartment 13. A detailed description of lamina forming materials, agents and other compounds appears later in the specification.

In operation in the environment of use, system 10 in one embodiment releases agent 16 housed in compartment 13 and soluble in the external fluid by fluid being imbibed into compartment 13 in a tendency towards osmotic equilibrium at a rate controlled by the permeability of laminate 12 and the osmotic pressure gradient across laminate 12 to continuously dissolve agent 16 which is osmotically pumped from system 10 through passageway 15 at a controlled and continuous rate over a prolonged period of time. System 10, in another embodiment, releases agent 16 that has limited solubility in the fluid and is mixed with an osmotically effective compound by fluid being imbibed through laminate 12 into compartment 13 in a tendency towards osmotic equilibrium at a rate controlled by the permeability of laminate 12 and the osmotic gradient across laminate 12 to continuously dissolve the osmotically effective compound to form a solution containing agent which is pumped from system 10 through passageway 15 at a controlled and continuous rate over a prolonged period of time.

System 10 of FIGS. 1A, 1B and 1C can be made into many embodiments including the presently preferred embodiment for oral use, that is, for releasing in the gastrointestinal tract either a locally or systemically acting therapeutic agent over a prolonged period of time. Oral system 10 can have various conventional shapes and sizes such as round with a diameter of 3/16 inch to ½ inch, or it can be shaped like a capsule having a range of sizes from triple zero to zero, and from 1 to 8.

FIG. 2 represents another system 10 manufactured according to the invention and designed for administering drug. In FIG. 2, system 10 is mounted on a drug receptor site 21, an arm of a human, for administering drug locally or systemically by absorption or drug penetration. System 10 is comprised of a non-toxic, laminate 12 surrounding and forming a half-circle shaped compartment, interior not shown, that contains an agent, or optionally a mixture of an agent and an osmotically effective compound. Laminate 12 is provided with a base ring 22 having a curvature that corresponds to the curvature of site 21 for securing system 10 to site 21. System 10 has a passageway positioned on its under surface, not shown, for releasing drug to site 21. Laminate 12 forms the under surface of system 10, which under surface is made of a semipermeable laminae forming material that is partially coated on its outer perimeter at base ring 22 with a thin layer of a non-toxic dermal-binding adhesive for holding system 10 on site 21. Moisture is drawn in from the body through semipermeable laminate 12. The half-circled surface of laminate 12 is made of a material that is substantially impermeable to fluid and substantially impermeable to agent to prevent loss of moisture that enters the compartment through the semipermeable laminated surface, and also to insure that all the agent is released through the passageway to site 21. System 10 is structured and operates as previously described and it administers drug at a controlled and continuous rate to site 21 for a prolonged period of time.

FIG. 3 shows an osmotic system 10 designed for placement in a vagina. System 10 has an elongated, cylindrical, self-sustaining shape with a rounded lead end 23 and it is equipped with a manually controlled cord 24 for easily removing system 10 from a vagina. System 10 is structurally identical with system 10 as described above and it also operates in a like manner. System 10 of FIG. 3 in one embodiment contains a drug designed for absorption by the vaginal mucosa to produce a local or systemic effect, and in another embodiment, it contains an odor reductant that emits an odor counteracting scent or fragrence in the vagina.

Referring to FIG. 4, an ocular therapeutic system 10 is seen in an eye 25 for administering drug at an osmotically metered dosage rate thereto. In FIG. 4, eye 25 is comprised of an upper eyelid 26 with eyelashes 27 and lower eyelid 28 with eyelashs 29. Eye 25 anatomically is comprised of an eyeball 30 covered for the greater part by sclera 31 and at its center area by cornea 32. Eyelids 26 and 28 are lined with an epithelial membrane or palpebral conjuctiva, and sclera 31 is lined with a bulbar conjunctiva that covers the exposed surface of eyeball 30. Cornea 32 is covered with a transparent epithelial membrane. The portion of the palpebral conjunctiva which lines upper eyelid 26 and the underlying portion of the bulbar conjunctiva defines an upper cul-de-sac, while that portion of the palpebral conjunctiva which lines lower eyelid 28 and the underlying portion of the bulbar conjunctiva defines a lower cul-de-sac. Ocular, osmotic system 10, seen in broken lines, is designed for placement in the upper or lower cul-de-sac. System 10 is seen in the lower cul-de-sac and it is held in place by the natural pressure of lower eyelid 28. System 10 contains an ophthalmic drug for release to eye 25 at a controlled and continuous rate over a prolonged period of time.

Ocular system 10 can have any geometric shape that fits comfortably in the cul-de-sac. Typical shapes include ellipsoid, bean, banana, circular, rectangular, doughnut, crescent and half-ring shaped devices. In cross-section, the devices can be doubly convex, concavo-convex, rectangular and the like, as the device in use will tend to conform to the shape of the eye. The dimensions of an ocular system can vary widely with the lower limit governed by the amount of drug to be supplied to the eye as well as by the smallest sized system that can be placed into the eye. The upper limit on the size of the system is governed by the space limitation in the eye consistent with comfortable retention in the eye. Satisfactory systems have a length of 4 to 20 millimeters, a width of 1 to 15 millimeters. The ocular system can contain from 0.15 micrograms to 100 milligrams of drug, or more, and it is made from materials non-toxic to the eye.

While FIGS. 1 through 4 are illustrative of various systems that can be made according to the invention, it is to be understood these systems are not to be construed as limiting, as the systems can take a wide variety of shapes, sizes and forms for delivering agent to different environments of use. For example, the systems include buccal, implant, anal, artificial gland, cervical, intrauterine, rectal, and ear systems. The systems also can be adapted for delivering an active agent in streams, aquariums, fields, factories, reservoirs, laboratory facilities, hot houses, transportation means, navel means, air and military means, hospitals, veterinary clinics, nursing homes, chemical reactions, and other environments of use.

DETAILED DESCRIPTION OF THE INVENTION

In accordance with the practice of the invention, it has now been found that osmotic delivery system 10 can be manufactured with a laminate(s) 12 comprised of at least two different laminae selected from the group of materials known as semipermeable, osmosis and reverse osmosis materials. The phrases "inert lamina forming material" and "unit or single semipermeable polymeric lamina forming material" as used for the present purpose means that each lamina is formed of a homopolymer or a copolymer. Laminae 19 and 20, or both in one embodiment are independently selected from semipermeable polymers which generically include lamina forming polysaccharides comprised of anhydroglucose units. In one embodiment, the polysaccharides are cellulose esters having a degree of substitution, D.S., on the anhydroglucose unit from greater than 0 up to 3 inclusive. By "degree of substitution" as used herein is meant the average number of hydroxyl groups on the anhydroglucose unit of the polymer replaced by a substituting group. Exemplary materials are represented by Formula 1:

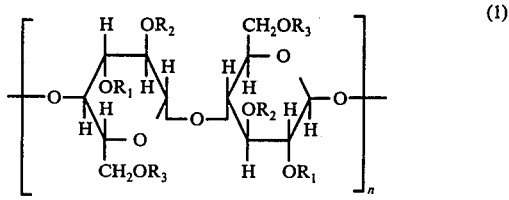
(1)

wherein $R_1$, $R_2$ and $R_3$ are the same or different and they are selected from the group consisting of hydrogen and acyl,

with at least one or all of $R_1$, $R_2$ and $R_3$ in the anhydroglucose unit either partially or completely substituted with the acyl moiety. The acyl moiety at $R_1$, $R_2$ and $R_3$ can be the same or different; and, $R_4$ is a member selected from the group consisting of hydrogen, alkyl groups of the straight or branched chain type having from 1 to 20 carbons and alkenyl groups that are straight or branched and have from 2 to 20 carbon atoms. Typical acyl moieties include alkanoyl and alkenoyl such as formyl, acetyl, propionyl, butyryl, hexanoyl, heptanoyl, octanoyl, undecanoyl, lauroyl, palmitoyl, stearoyl, oleoyl, and isomeric forms thereof; an $n$ in a presently preferred embodiment is a positive number greater than 5.

Representative materials embraced by Formula 1 include polymeric cellulose esters such as mono, di, and tricellulose acylates. Exemplary polymers include cellulose acetate having a D.S. of 1 and an acetyl content of up to 21%; cellulose diacetate having a D.S. of 2 and an acetyl content of 21 to 35%; cellulose triacetate having a D.S. of 3 and an acetyl content of 35 to 44.8%; cellulose propionate having a D.S. of 1.8 and a propionyl content of 38.5%; cellulose acetate propionate having an acetyl content of 1.5 to 7% and a propionyl content of 39 to 42%; cellulose acetate propionate having an acetyl content of 2.5 to 3%, an average combined propionyl content of 39.2 to 45% and a hydroxyl content of 2.8 to 5.4%; cellulose acetate butyrate having a D.S. of 1.8, an acetyl content of 13 to 15%, and a butyryl content of 34 to 39%; cellulose acetate butyrate having an acetyl content of 2 to 29.5%, a butyryl content of 17 to 53%, and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, cellulose triheptylate, cellulose tricaprylate, cellulose trioctanoate and cellulose tripropionate; cellulose diesters having a lower degree of substitution and prepared by the hydrolysis of the corresponding triester to yield cellulose diacylates having a D.S. of 2.2 to 2.6 such as cellulose disuccinate, cellulose dipalmitate, cellulose dioctanoate, cellulose dicaprylate and cellulose dipentanoate and esters prepared from acyl anhydrides or acyl acids in an esterification reaction to yield esters containing acyl attached to the same cellulose polymer such as cellulose acetate valerate, cellulose acetate succinate, cellulose propionate succinate, cellulose acetate octanoate, cellulose valerate palmitate, cellulose acetate palmitate and cellulose acetate heptanoate. Generally, the laminae useful for forming the laminate wall will have a fluid permeability of $10^{-5}$ to $10^{-1}$ (cc·mil/cm²·hr·atm), expressed per atmosphere of hydrostatic or osmotic pressure difference across the lamina at the temperature of use while possessing a high degree of impermeability to solute are useful for the purpose of the invention. The polymers described above are known to the art or they can be prepared according to the procedures in *Encyclopedia of Polymer Science and Technology*, Vol. 3, pages 325 to 354, 1964, published by Interscience Publishers Inc., New York.

Laminae 19 or 20 or both also can be independently selected from different unit materials embraced by Formula 2 as follows:

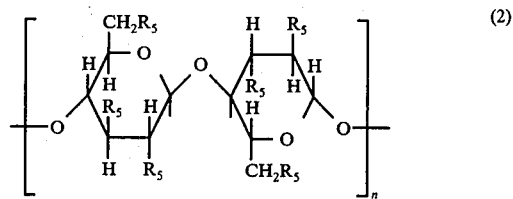
(2)

wherein $R_5$ is a member selected from the group consisting of hydroxyl; alkoxy; alkoxy substituted with a member selected from the group consisting of alkyl, alkoxy, halogen and cyano; alkylcarbonate; alkylcarbamate; alkylsulfonate; alkylsulfamate; oxalkyleneoxycarboalkyl; acyloxy including alkanoyloxy, alkenoyloxy and aroyloxy; alkanoyloxy substituted with an alkoxy, halogen, carboalkyl, carboalkoxy and cyanoalkoxy; aroyloxy substituted with a halo, carboxy, carboalkyl and cyano; furoyloxy, and $n$ is a positive integer greater than 5, usually 10 to 3 × 10⁶.

Exemplary groups representative of $R_5$ of Formula 2 are as follows: by "alkyl" is meant straight or branched chain alkyl radicals of 1 to 20 carbon atoms inclusive, such as methyl, ethyl, n-propyl, iso-propyl, n-butyl, sec-butyl, pentyl, neo-pentyl, n-hexyl, iso-hexyl, heptyl, 4,4-dimethyl pentyl, 2,2,4-trimethylpentyl, and nonyl. By "alkenyl" is meant straight or branched chain alkenyl groups of 2 to 20 carbons such as 1-propenyl, 2-propenyl or allyl, 1-butenyl, 2-butenyl, 1-pentenyl, and the corresponding positional isomers such as 1-isobutenyl, 2-isobutenyl, 2-sec-butenyl, 2-methyl-1-butenyl, 2-methyl-2-pentyenyl and 2,3-dimethyl-3-hexenyl. The term "alkoxy" as used for $R_5$ included the straight and branched chain alkoxy groups having 1 to 20 carbons inclusive, for example, methoxy, ethoxy, propoxy, butoxy, n-pentoxy, n-hexoxy, isopropoxy, 2-butoxy, isobutoxy, 3-pentoxy, and n-octoxy. Exemplary halogen include fluorine, chlorine and bromine. Exemplary aryl include phenyl and naphthyl. Representative alkylene as a linking moiety within a substituent are alkylene of 2 to 10 carbons such as 1,2-ethylene, 1,3-propylene, 1,2-propylene, 1,4-butylene, 1,5-pentylene, 1,6-hexylene, 1,7-heptylene and 1,10-decylene. Exemplary alkanoyloxy, alkenoyloxy and aroyloxy include formyloxy, acetyloxy, propionyloxy, valeryloxy, heptanoyloxy, octanoyloxy, undecanoyloxy, lauroyloxy, palmitoyloxy, stearoyloxy, oleoyloxy, acryloyloxy, methacryloyloxy, crotomyloxy, 3-butenoyloxy, benzoyloxy, phenylacetyloxy, cinnamoyloxy, naphthoyloxy, p-ethoxybenzyloxy, alloxyphenylacetyloxy, furoyloxy, p-nitrobenzoyloxy and chlorophenoxyacetyloxy.

The lamina forming materials embraced by Formula 2 include polysaccharide materials having a degree of substitution on the anhydroglucose unit greater than from 0 up to 3 inclusive with the substituents at $R_5$ the same or different and bonded to a common mer. The materials can be polymeric cellulose esters or polymeric cellulose ethers. The monomeric unit can be substituted with like ester groups, with different ester groups, with like ether groups, with different ether groups and with different ester and ether groups bonded to the same polymer to give a homopolymer or copolymer. Typical materials represented by Formula 2 include cellulose acetate acetoacetate, cellulose acetate chloroacetate, cellulose acetate furoate, dimethoxyethylcellulose acetate, cellulose acetate carboxymethoxypropionate, cellulose acetate phthalate, cellulose butyrate naphthylate, cellulose acetate benzoate, methylcellulose acetate, methylcyanoethyl cellulose, cellulose acetate methoxyacetate, cellulose acetate, cellulose acetate ethoxyacetate, cellulose acetate dimethylsulfamate, ethylcellulose dimethylsulfamate, cellulose acetate p-toluene sulfonate, cellulose acetate methylsulfonate, cellulose acetate butylsulfonate, cellulose acetate dimethylaminoacetate, cellulose acetate ethyloxalate, cellulose resinate, cellulose acetate methylcarbonate, cellulose acetate ethylcarbonate, cellulose acetate methylcarbamate, and cellulose acetate ethylcarbamate.

The semipermeable laminae forming materials also include cellulose ethers such as alkylcellulose, methylcellulose, ethylcellulose, ethylmethylcellulose, hydroxyethylcellulose, hydroxypropylcellulose, hydroxyethyl methylcellulose, hydroxypropyl methylcellulose, ethylhydroxy ethylcellulose, hydroxybutyl methylcellulose, cyanoethylcellulose, benzylcellulose, sodium carboxymethylcellulose, sodium carboxymethylhydroxy ethylcellulose, carbamoylethylcellulose, carboxyethylcellulose, phenylcellulose, benzylhydrylcellulose, tritylcellulose, hexylpropylcellulose, carboxylbenzyl cellulose, and 2-carboxylbenzoyloxy propylcellulose. Methods for preparing the cellulose ethers are disclosed in *Encyclopedia of Polymer Science and Technology*, Vol. 3, pages 459 to 549, 1964, published by Interscience Publishers, Inc., New York.

Other semipermeable materials include acylated polysaccharides and acylated starches such as agar-agar acetate, acylated alginates, amylose triacetate, beta glucan acetate, beta glucan triacetate, acetyl alginate, triacetate of locust bean gum, alkanoyl carrageenin, acylated tragacanth, esterified gum karaya, cellulose derivatives substituted with an inorganic moiety such as a nitro group, hydroxylated ethylene vinylacetate, aromatic nitrogen containing polymeric materials that exhibit permeability to aqueous fluids and substantially no passage to solute, semipermeable membranes made from polymeric epoxides, copolymers of alkylene oxides and alkyl glycidyl ethers, polyvinyl acetate, cross-linked polyvinyl acetate, polyurethanes, film forming materials as disclosed by Loeb and Sourirajan in U.S. Pat. No. 3,133,132, cross-linked derivatives of polyvinyl alcohol, polyvinyl butyrate, ionically associated polyelectrolytes formed by the coprecipitation of a polycation and a polyanion as described in U.S. Pat. Nos. 3,276,586; 3,541,005; 3,541,006; 3,546,142; and 3,173,876; polystyrene derivatives such as poly(sodium styrene sulfonate) and poly(vinylbenzyltrimethyl ammonium chloride), polyesters, polyamides and polyacrylates. These semipermeable materials and other semipermeable materials are known to the art and disclosed in *Handbook of Common Polymers* by Scott, J. R. and Roff, W. J., 1971, published by CRC Press, Cleveland, Ohio.

Suitable laminae forming materials for manufacturing an osmotic system can be selected from the above materials according to the criterion disclosed in U.S. Pat. Nos. 3,845,770 and 3,916,899. This criterion consists in first calculating for a laminate that is to be selected, the permeability to fluid necessary to deliver an amount of agent $Q_p$, in mg, in time $t$, in hours, from a device having a total laminate area A, in cm$^2$, a laminate thickness $h$, in mils, with the agent having a solubility in the fluid S, in mg/ml (solution), and the agent having an osmotic pressure in the device of $\pi$, in atm. The value $k$ is expressed in units (cm$^3$/cm$^2$) · (mil/hr·atm), and it is calculated from Equation 1.

$$k = h/S\,A \cdot Q_p/t \cdot 1/\pi \tag{1}$$

Then, after having calculated the desired laminate permeability $k$ from Equation 1, laboratory measurements are made to identify laminae materials capable of forming a laminate having a permeability $k_o$ substantially equivalent to the calculated permeability $k$. The measurements are carried out by using a standard osmosis cell and measuring the rate of fluid flow through a laminate made of laminae forming materials having a known composition and thickness. The flow rate is determined by measuring fluid transport from a first chamber containing a fluid free of agent through a laminate that separates it from a second chamber housing a solution containing a known concentration of agent that exhibits an osmotic gradient across the laminate. Sometimes the chamber contains an osmotically effective compound which is used as osmotic driving agent in the final device. The flow measurement is performed by adding to the first chamber the fluid and then adding to the second chamber, equipped with a stirring bar, the same fluid containing agent, and optionally containing the additional osmotic agents. The first chamber is connected through a conduit to a reservoir containing a supply of fluid and the second chamber is connected to a vertically positioned tube of known diameter and calibrated with indicia that indicate the amount of fluid in the tube. In operation, fluid flows from the first chamber through the laminate into the second chamber by osmosis causing the solution to rise in the tube over time, $t$, to give a volume displacement, $\Delta V$, during a time interval, $\Delta t$. The volume, $\Delta V$, is read on the tube calibrated in cm$^3$, and the time interval, $\Delta t$, is measured with a stopwatch. The value $k_o\pi_o$ in cm$^3$·mil/cm$^2$·hr for the laminate with permeability, $k_o$, for the agent solution with an osmotic pressure, $\pi_o$, is calculated from Equation 2, and wherein $A_o$ is the area of the membrane, in the diffusion cell, and $h_o$ is the thickness of this membrane.

$$k_o\pi_o = \Delta V/\Delta t \cdot h_o/A_o \tag{2}$$

If the measured value, $k_o$, approximates the calculated value, $k$, the laminate can be used for manufacturing the osmotic device. Other procedures and devices useful for measuring fluid permeability and osmotic flow are disclosed in *J. App. Poly. Sci.*, Vol. 9, pages 1341 to 1362, 1965; and in *Yale J. Biol. Med.*, Vol. 42, pages 139 to 153, 1970.

The physical and chemical integrity and the inertness of the above materials can be ascertained by those skilled in the art by using the procedures described below. These procedures are the lamina weight loss and the osmosis procedures. The weight loss procedure is carried out with a lamina that is cast from solution or optionally melt pressed. The lamina is solution cast with a Gardner film-casting knife on a clean glass plate at room temperature with the solution removed by evaporation in an oven at elevated temperatures until the lamina is dry. Next, the lamina is removed from the glass and cut into strips 1 to 10 cm in length, 1 to 10 cm in width and having a thickness of 1 to 10 mils. Then, after all the strips are cut to have the same area and weight, they are placed in a glass container filled with a solution consisting of a known concentration of agent formulated with the fluid of the environment of use. The temperature of the container is made to correspond to the temperature of the environment where an osmotic system formed with the lamina will be placed for releasing agents. At regular time intervals, strips are taken form the solution, rinsed in distilled water, dried in an oven, usually 50° C for 24 hours, and weighed. The weight of a single strip repeatedly introduced into the solution, or the weight of many strips consecutively removed at different time intervals are indicated along the ordinate, plotted as a function of time indicated along the abscissa, such as $t_1$, $t_2$, $t_3$, etc. as shown in FIG. 5. In FIG. 5, line 1 represents the results obtained for a lamina that maintains its physical and chemical integrity when exposed to agent solution. That is, the lamina does not lose any weight over time and demonstrates inertness in the presence of agent solution. In the same figure, line 2 represents a lamina which upon exposure to agent solution, demonstrates a weight loss and is undesirable for making an osmotic system.

Figure 6:
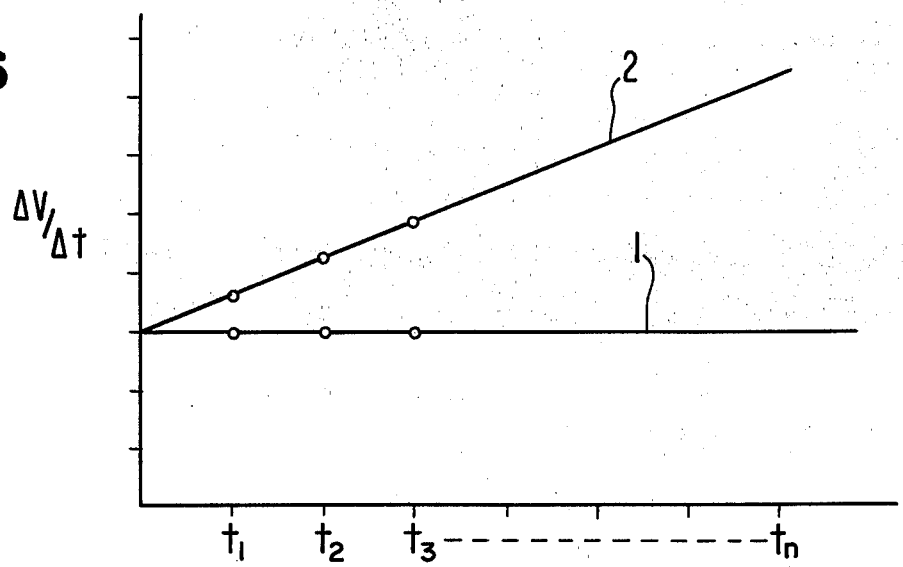
FIG. 6 is a graph comparing the permeability of a laminate that maintains its integrity in the presence of fluid with a laminate that slowly loses its integrity in the presence of fluid.

In the osmosis procedure, the rate of fluid flow through a laminate is measured and it is performed using an osmosis cell. The purpose of the procedure is to ascertain, (1) if a given laminate maintains its integrity in the presence of fluid and agent. The procedure is carried out using the cell according to the above described procedure with the volume of solution, $\Delta V$, rising in the tube attached to chamber 2 measured and plotted as a function of time, $t$. The data obtained for two different laminates are shown in FIG. 6. In FIG. 6, line 1 represents a laminate that maintains its integrity in the presence of fluid and agent. That is, since the rate of fluid flow is substantially constant, the laminate does not undergo any substantial change over time, $t$. Line 2 shows the fluid flux, $\Delta V/\Delta t$, through a laminate where the rate is continually increasing over time. This change indicates the laminate does not maintain its integrity in the presence of fluid and agent. For those applications where a change in flux is unwanted, a different laminate should be selected for the system. Using the above techniques, one versed in the art would use the weight loss and osmosis procedures for deciding if the fluid and agent adversely effect the laminate and for determining if a laminate is suited for a particular application. This procedure also can be used to ascertain the properties of laminae.

Additional scientific criterions that can be used by those skilled in the art for selecting laminate materials that have increased inertness, include the following: (a) the polymeric materials forming the laminae of the laminate have a high degree of substitution, for example, the materials have undergone etherification or esterification particularly acylation towards or to completion with the laminae demonstrating increased resistance to hydrolysis and increased rejection of agent, (b) the laminae of the laminate exhibits a flux decrease with increasing molecular size of the substituting groups, such as an ether or ester group, (c) the laminae of the laminate exhibits a flux decrease proportional to the increase in size of the substituents, for example, the decrease occurs as the number of carbon atoms increase in a hydrocarbon moiety such as an alkyl or alkoxy moiety, (d) the laminae of the laminate exhibits increased stability with an increase in the degree or substitution of hydrophobic ether and larger hydrophobic ester groups with an accompanying decrease in the degree of substitution of smaller hydrophilic ester groups, and (e) the laminae of the laminate exhibits a flux decrease as the number of polar, ionic groups decrease. *J. App. Poly. Sci.*, Vol. 9, pages 1341 to 1362, 1965.

The expression "passageway" as used herein comprises means and methods suitable for releasing the agent from the system. The expression includes an aperture, orifice or bore through the laminate formed by mechanical procedures, or by eroding an erodible element, such as a gelatin plug, in the environment of use. A detailed description of osmotic passageways and the maximum and minimum dimensions for a passageway are disclosed in U.S. Pat. No. 3,845,770 and in U.S. pat. No. 3,916,899.

The osmotically effective compounds that can be used for the purpose of the invention include inorganic and organic compounds that exhibit an osmotic pressure gradient against an external fluid across laminate 12 of the device. The compounds, also known as osmagents, are mixed with an agent that has limited solubility in the external fluid with the compound forming a saturated solution containing agent that is osmotically delivered from the device. The phrase "limited solubility" as used herein means the agent has a solubility of about less than 1% by weight in the external fluid. The compounds are used by homogeneously or heterogenously mixing the compound or a mixture of compounds with an agent, either before they are charged into the reservoir, or by self-mixing after they are charged into the reservoir. In operation, these compounds attract fluid into the device producing a solution of compound which is delivered from the device concomitantly transporting undissolved and dissolved agent to the exterior of the device. Osmotically effective compounds useful for the present purpose include magnesium sulfate, magnesium chloride, sodium chloride, lithium chloride, potassium sulfate, sodium carbonate, sodium sulfite, lithium sulfate, potassium chloride, calcium bicarbonate, sodium sulfate, calcium sulfate, potassium acid phosphate, calcium lactate, d-mannitol, urea, inositol, magnesium succinate, tartaric acid, carbohydrates such as raffinose, sucrose, glucose, α-d-lactose monohydrate, and mixtures thereof. The compound is initially present in excess and it can be in any physical form such as particle, crystal, pellet, tablet, strip, film or granule. The osmotic pressure of saturated solutions of various osmotically effective compounds and for mixtures of compounds at 37° C, in water, is listed in Table 1. In the table, the osmotic pressure $\pi$, is in atmospheres, ATM. The osmotic pressure is measured in a commercially available osmometer that measures the vapor pressure difference between pure water and the solution to be analyzed, and according to standard thermodynamic principles, the vapor pressure difference is converted into osmotic pressure. In Table 1, osmotic pressures of from 20 ATM to 500 ATM are set forth; of course, the invention includes the use of lower osmotic pressures from zero, and higher osmotic pressures than those set forth by way of example in Table 1. The osmometer used for the present measurements is identified as Model 302B, Vapor Pressure Osmometer, manufactured by the Hewlett Packard Co., Avondale, Penna.

TABLE 1

| COMPOUND OR MIXTURE | OSMOTIC PRESSURE ATM |
|---|---|
| Lactose-Fructose | 500 |
| Dextrose-Fructose | 450 |
| Sucrose-Fructose | 430 |
| Mannitol-Fructose | 415 |
| Sodium Chloride | 356 |
| Fructose | 355 |
| Lactose-Sucrose | 250 |
| Potassium Chloride | 245 |
| Lactose-Dextrose | 225 |
| Mannitol-Dextrose | 225 |
| Dextrose-Sucrose | 190 |
| Mannitol-Sucrose | 170 |
| Sucrose | 150 |
| Mannitol-Lactose | 130 |
| Dextrose | 82 |
| Potassium Sulfate | 39 |
| Mannitol | 38 |
| Sodium Phosphate Tribasic . 12H$_2$O | 36 |
| Sodium Phosphate Dibasic . 7H$_2$O | 31 |
| Sodium Phosphate Dibasic . 12H$_2$O | 31 |
| Sodium Phosphate Dibasic Anhydrous | 29 |
| Sodium Phosphate Monobasic . H$_2$O | 28 |

The expression "active agent" as used herein broadly includes any compound, composition of matter or mixture thereof, that can be delivered from the system to produce a beneficial and useful result. The agent can be soluble in a fluid that enters the compartment and functions as an osmotically effective solute or it can have limited solubility in the fluid and be mixed with an osmotically effective compound soluble in fluid that is delivered from the system. The active agent includes pesticides, herbicides, germicides, biocides, algicides, rodenticides, fungicides, insecticides, anti-oxidants, plant growth promoters, plant growth inhibitors, preservatives, disinfectants, sterilization agents, catalysts, chemical reactants, fermentation agents, foods, food supplements, nutrients, cosmetics, drugs, vitamins, sex sterilants, fertility inhibitors, fertility promoters, air purifiers, micro-organism attenuators, and other agents that benefit the environment of use.

In the specification and the accompanying claims, the term "drug" includes any physiologically or pharmacologically active substance that produces a localized or systemic effect or effects in animals, including mammals, humans and primates, avians, domestic household, sport or farm animals such as sheep, goats, cattle, horses and pigs, for administering to laboratory animals such as mice, rats and guinea pigs, and to fishes, reptiles and zoo animals. The active drug that can be delivered includes inorganic and organic compounds without limitation, those materials that act on the central nervous system such as hypnotics and sedatives, including pentobarbital sodium, phenobarbital, secobarbital, thiopental and mixtures thereof, heterocyclic hypnotics such as dioxopiperidines and glutarimides, hypnotics and sedatives such as amides and ureas, exemplified by diethylisovaleramide and $\alpha$-bromoisovaleryl urea, hypnotic and sedative urethanes and disulfanes, psychic energizers such as isocarboxazid, nialamide, phenelzine, imipramine, tranylcypromine and pargylene, tranquilizers such as chlorpromazine, promazine, fluphenazine, reserpine, deserpidine, meprobamate, benzodiazepines such as chlordiazepoxide, anticonvulsants such as primidone, enitabas, diphenylhydantoin, ethltion, pheneturide and ethosuximide, muscle relaxants and antiparkinson agents such as mephenesin, methocarbomal, trihexylphenidyl, biperiden, levo-dopa also known as L-dopa and L-$\beta$-3-4-dihydroxypehnylalanine, analgesics such as morphone, codeine, meperidine, nalorphine, antipyretics and anti-inflammatory agents such as aspirin, salicylamide, colchicine and sodium salicylamide, local anesthetics such as procaine, lidocaine, naepaine, piperocaine, tetracaine and dibucane, antispasmodics and muscle contractants such as atropine, scopolamine, methscopolamine, oxyphenonium, papaverine, prostaglandins such as PGE$_1$, PGE$_2$, PGF$_{1\alpha}$ PGF$_{2\alpha}$ and PGA, anti-microbials such as penicillin, tetracycline, oxytetracycline, chlorotetracycline, chloramphenicol and sulfonamides, anti-malarials such as 4-aminoquinolines, 8-aminoquinolines and pyrimethamine, hormonal agents such as prednisolone, cortisone, cortisol and triamcinolone, androgenic steroids such as methyltestosterone, and fluoxmesterone, estrogenic steroids such as 17$\beta$-estradiol, $\alpha$-estradiol, estriol, $\alpha$-estradiol 3-benzoate, and 17-ethynyl estradiol-3-methyl ether, progestational steriods such as progesterone, 19-nor-pregn-4-ene-3,20-dione, 17-hydroxy-19-nor-17-$\alpha$-pregn-5(10)-ene-20-yn-3-one, 17 $\alpha$-ethynyl-17-hydroxy-5(10)-estren-3-one, and 9$\beta$,10 $\alpha$-pregna-4,6-diene-3,20-dione, sympathomimetic drugs such as epinephrine, amphetamine, ephedrine and norepinephrine, cardiovascular drugs such as procainamide, procainamide sulfate, procainamide hydrochloride, procainaminde salts, amyl nitrile, nitroglycerin, dipyredamole, sodium nitrate and mannitol nitrate, diuretics such as chlorathiazide, acetazolamide, methazolamide and flumethiazide, antiparasitics such as bephenium, hydroxynaphthoate, dichlorophen and dapsone, neoplastics such as mechlorethamine, uracil mustard, 5-fluorouracil, 6-thioguanine and procarbazine, hypoglycemic drugs such as insulin, isophane insulin, protamine zinc insulin suspension, globin zinc insulin, extended insulin zinc suspension, tolbutamide, acetohexamide, tolazamide and chlorpropamide, nutritional agents such as ascorbic acid, niacin, nicotinamide, folic acid, choline, biotin, pantothenic acid, and vitamin B$_{12}$, essential amino acids, essential fats, eye drugs such as pilocarpine, pilocarpine salts such as pilocarpine nitrate, pilocarpine hydrochloride, dichlorphenamide, atropine, atropine sulfate, scopolamine and eserine salicylate, and electrolytes such as calcium gluconate, calcium lactate, potassium chloride, potassium sulfate, sodium chloride, potassium fluoride, ferrous lactate, ferrous gluconate, ferrous sulfate, ferrous fumurate and sodium lactate. The beneficial drugs are known to the art in *Pharmaceutical Sciences,* by Remington, 14th Ed., 1970, published by Mack Publishing Co., Easton, Penna.; and in *The Pharmacological Basis of Therapeutics,* by Goodman and Gilman, 4th Ed., 1970, published by The MacMillian Company, London.

The drug can also be in various forms, such as uncharged molecules, molecular complexes, pharmacologically acceptable salts such as hydrochlorides, hydrobromides, sulfate, laurylate, palmitate, phosphate, nitrate, borate, acetate, maleate, tartrate, oleate, and salicylate. For acidic drugs, salts of metals, amines or organic cations, for example quaternary ammonium can be used. Derivatives of drugs such as esters, ethers and amides which have solubility characteristics suitable for use herein can be used alone or mixed with other drugs. Also, a drug that is water insoluble can be used in a form that is a water soluble derivative thereof to effectively serve as a solute, and on its release from the device, is converted by enzymes, hydrolyzed by body pH or other metabolic processes to the original form, or to a biologically active form. The agent can be in the reservoir as a solution, dispersion, paste, cream, particle, granule, emulsion, suspension or powder. Also, the agent can be mixed with a binder, dispersant, emulsifier or wetting agent and dyes.

The amount of agent present in the system is initially in excess of the amount that can be dissolved in the fluid that enters the compartment. Under this physical state when the agent is in excess, the system will osmotically operate to give a substantially constant rate of release. The rate of agent release pattern can also be varied by having different amounts of agent in the reservoir to form solutions containing different concentrations of agent for delivery from the system. Generally, the system can house from 0.05 ng to 5 grams or more, with individual systems containing for example, 25 ng, 1 mg, 5 mg, 250 mg, 500 mg, 1.5 g, and the like.

The solubility of an agent in an external fluid can be determined by various art known techniques. One method consists in preparing a saturated solution comprising the external fluid plus the agent as ascertained by analyzing the amount of agent present in a definite quantity of the fluid. A simple apparatus for this purpose consists of a test tube of medium size fastened upright in a water bath maintained at constant temperature and pressure, for example, one atmosphere, in which the fluid and agent are placed and stirred by a motor driven rotating glass spiral. After a given period of stirring, a definite weight of the fluid is analyzed and the stirring continued for an additional period of time. If the analysis shows no increase of dissolved agent after successive periods of stirring, in the presence of excess solid agent in the fluid, the solution is saturated and the results are taken as the solubility of the product in the fluid. If the agent is soluble and added osmotically effective compound is not needed; if the agent has limited solubility in the fluid, then an osmotically effective compound can be incorporated into the device. Numerous other methods are available for the determination of the solubility of an agent in a fluid. Typical methods used for the measurement of solubility are chemical analysis, ultra violet spectometry, density, refractive index and electrical conductivity. Details of various methods for determining solubilities are described in *United States Public Health Service Bulletin,* No. 67 of the Hygienic Laboratory; *Encyclopedia of Science and Technology,* Vol. 12, pages 542 to 556, 1971, published by McGraw-Hill, Inc.; and *Encyclopaedic Dictionary of Physics,* Vol. 6, pages 547 to 557, 1962, published by Pergamon Press, Inc.

The systems of the invention are manufactured by standard techniques. For example, in one embodiment, the agent and other ingredients that may be housed in the compartment and a solvent are mixed into a solid, semisolid or gel form by conventional methods such as ballmilling, calendering, stirring, or rollmilling and then pressed into a preselected shape. The laminate forming the system can be applied by molding, spraying or dipping the pressed shape into the materials. In another embodiment, laminae can be cast into films, shaped to the desired dimensions, an exterior lamina sealed to an interior lamina to define a laminate that surrounds a compartment that is filled with agent and then closed. The system also can be manufactured with an empty compartment that is filled through the passageway. The laminae forming the laminate can be joined by various joining techniques such as high frequency electronic sealing that provides clean edges and firmly formed laminates. Another, and presently preferred, technique that can be used is the air suspension procedure. This procedure consists in suspending and tumbling the agent in a current of air and a lamina composition until the lamina is applied to the agent. The procedure is repeated with a different lamina to form the laminate. The air suspension procedure is described in U.S. Pat. No. 2,799,241; *J. Am. Pharm. Assoc.,* Vol. 48, pages 451 to 459, 1959; and *ibid.,* Vol. 49, pages 82 to 84, 1960. Other lamina forming techniques such as pan coating can be used in which the laminae are deposited by successive spraying of the polymer solution with the agent tumbling in the rotating pan. Other standard manufacturing procedures are described in *Modern Plastics Encyclopedia,* Vol. 46, pages 62 to 70, 1969; and in *Pharmaceutical Sciences,* by Remington, Fourteenth Edition, pages 1626 to 1678, 1970, published by Mack Publishing Company, Easton, Penna.

Exemplary solvents suitable for manufacturing the laminated wall include inert inorganic and organic solvents that do not adversely harm the wall forming materials and the final laminate. The solvents broadly include members selected from the group consisting of aqueous solvents, alcohols, ketones, esters, ethers, aliphatic hydrocarbons, halogenated solvents, cycloaliphatic, aromatics heterocyclic solvents and mixtures thereof. Typical solvents include acetone, diacetone alcohol, methanol, ethanol, isopropyl alcohol, butyl alcohol, methyl acetate, ethyl acetate, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclooctane, benzene, toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol.

The following examples are merely illustrative of the present invention and they should not be considered as limiting the scope of the invention in any way, as these examples and other equivalents thereof will become apparent to those versed in the art in the light of the present disclosure, the drawing and the accompanying claims.

EXAMPLE 1

An osmotic, ocular therapeutic system for the controlled and continuous delivery of pilocarpine nitrate at a rate of 105 μg/hr from a system having a unit, laminated wall with a total area of 1.2 cm² and a laminate thickness of 3 mils, with the pilocarpine nitrate having a solubility of 250 mg/ml in water, and with the ocular system designed in the form of an elliptical shaped system is constructed as follows: first, to an elliptical shaped drug core consisting of pilocarpine nitrate is applied, from dimethyl formamide solvent, a 1 mil thick, $h_1$, lamina of inert, ophthalmologically acceptable semipermeable polyurethane to yield an inner lamina having a $k\pi_1$ of $0.36 \times 10^{-3}$ cc·mil/hr·cm². Next, to the total outer surface of the polyurethane lamina is applied, in laminar contacting relation, from a 5% polymer solution in acetone:water in the ratio of 90:10, a 2 mil thick, $h_2$, lamina of inert, ophthalmologically acceptable semipermeable cellulose acetate having an acetyl content of 32% to yield a lamina that forms an integral unit laminate with the polyurethane lamina. The cellulose acetate lamina had a measured $k\pi_2$ of 0.03 cc·mil/hr·cm². Finally, an osmotic passageway is drilled through the laminate for osmotically releasing ophthalmic drug from the system. The passageway had a diameter of 2 mils.

The osmotic system releases a therapeutically effective amount of pilocarpine nitrate according to relations 1 through 4 as follows:

$$h_T/k\pi_T = h_1/k\pi_1 + h_2/k\pi_2 \tag{1}$$

wherein $h_T$ is the total thickness of the laminate, $h_1$ is the thickness of the polyurethane lamina, $h_2$ is the thickness of the cellulose acetate lamina, $k\pi_T$ is the osmotic pressure of the drug in the compartment of the system times the permeability of the laminate to water or eye fluid, and $k\pi_1$ and $k\pi_2$ represent the osmotic pressure of the drug in the compartment times the permeability of lamina$_1$ and lamina$_2$ to water or eye fluid respectively.

$$\frac{3}{k\pi_T} = \frac{1}{0.36 \times 10^{-3}} + \frac{2}{0.03} \tag{2}$$

$$k\pi_T = 1.05 \times 10^{-3} \text{ cc·mil/hr·cm}^2$$

The amount of drug delivered in μg/hr for the osmotic therapeutic system is calculated as follows:

$$dm/dt = S \times A \times K\pi_T/h_T \tag{3}$$

wherein S is the solubility of the drug in water or eye fluid and A is the total area of the laminated wall in cm²:

$$\frac{dm}{dt} = \frac{250 \times 1.2 \times 1.05 \times 10^{-3}}{3} = 105 \text{ μg/hr} \tag{4}$$

The osmotic system when placed in the cul-de-sac of an adult, human eye administers 105 μg/hr of pilocarpine nitrate with the system maintaining its uniformity and configuration during the osmotic dispensing period.

EXAMPLE 2

The ocular, osmotic therapeutic system described in Example 1 is manufactured in this example with all conditions as previously described except that the drug in the compartment is replaced with an ophthalmic drug that is a member selected from the group consisting of idoxuridine, phenylephrine, pilocarpine, hydrochloride, eserine, carbachol, phospholine iodine, demecarium bromide, cyclopentolate, homatropine, scopolamine and epinephrine.

EXAMPLE 3

An osmotic therapeutic system manufactured in the form of an oral, osmotic device for releasing potassium chloride in the gastrointestinal tract was made as follows: first, 500 mgs of potassium chloride was compressed by standard techniques with a 3/8 inch punch into a compressed mass having a total area of 2.3 cm². The mass was then laminated by surrounding it with a laminate comprised of an inner and outer laminae. The inner lamina was formed of non-erodible, inert 70 minutes hydrolyzed polyvinyl acetate applied to the mass by the air suspension techniques described in *J. Pharm. Sci.*, Vol. 53, No. 8, pages 877 to 881, 1964 and ibid., Vol. 53, No. 8, pages 953 to 955, 1964. A 5% polymer solution in 200 proof ethanol:water in the ratio of 90:10, volume to volume, was used to form the lamina which had a final thickness $h_1$ of 1 mil and a $k\pi_1$ of 0.1 cm³·mil/cm²·hr.

Next, an outer lamina that maintains its integrity in the environment of use and consisting of semipermeable polymeric cellulose acetate having an acetyl content of 32% was laminated onto the total exposed surface of lamina $h_1$ to form a laminated wall that surrounded the potassium chloride drug compartment. The cellulose acetate was intimately applied to lamina $h_1$ from a 5% solution in acetone:water in the proportion of 89:11, weight to weight. The outer lamina had a thickness $h_2$ of 3.6 mils and a $k\pi_2$ of 0.27 cm³·mil/cm²·hr.

The final laminated wall of the osmotic system had a thickness $h_T$ of 4.6 mils. An osmotic passageway was drilled through the laminated wall and it had a diameter of 9 mils. The system had a controlled and continuous rate of release of 31.52 mgs/hr with a variation of about ±5%. The rate of release was calculated according to relations 1 through 4 as follows:

$$h_T/k\pi_T = h_1/k\pi_1 + h_2/k\pi_2 \tag{1}$$

$$4.6/k\pi_T = 1/0.1 + 3.6/0.27 \tag{2}$$

$$k\pi_T = 0.197 \text{ cm}^3\text{·mil/cm}^2\text{·hr}$$

$$dm/dt = S \times A \times k\pi_T/h_T \tag{3}$$

wherein S is the solubility of KCl in mg/ml at 37° C, and A is the total laminated area exposed to the environment:

$$dm/dt = 320 \times 2.3 \times 0.197/4.6 \tag{4}$$

$$dm/dt = 31.52 \text{ mg/hr}$$

EXAMPLE 4

A plurality of osmotic therapeutic systems are manufactured according to the procedure of Example 3 wherein the conditions are as described except that the drug of Example 3 was replaced with an orally administerable drug selected from the group consisting of methazolamide, ethoxyolamide, diazepam, amitriptylene hydrochloride, imipramine hydrochloride, naicin, benzthiazide, aminophylline, chlorothiazide, tolbutamide, tolazamide, chloropropamide, procainamide hydrochloride, colchicine and atropine.

EXAMPLE 5

An osmotic therapeutic system for delivering NaCl at an osmotically controlled rate was manufactured according to the procedure of Examples 1 and 3 with all conditions as previously described except that the laminated wall surrounding the compartment comprised three lamina in intimate, total laminar arrangement to form a unit wall. In this system, the lamina facing the drug compartment consisted of polymeric cellulose acetate having an acetyl content of 38.3%, a thickness $h_1$ of 0.5 mils and a $k\pi_1$ of 0.054 cc·mils/hr·cm². The lamina was formed from a 4% polymer solution in acetone. A section lamina $h_2$ consisting of polymeric cellulose acetate having an acetyl content of 32.0% was laminated from a 4% polymeric solution having a solvent system consisting of acetone:water in the proportion of 89:11, weight to weight, directly onto lamina $h_1$. Lamina $h_2$ had a thickness of 3 mils and a $k\pi_2$ of 0.26 cm³·mil/cm²·hr. Next, a third lamina $h_3$ was laminated to the free surface of lamina $h_2$ to form laminated wall $h_T$. Lamina $h_3$ consisted of 90 minutes hydrolyzed semipermeable polyvinyl acetate and it was formed from a 4% polymeric solution in ethanol:water in the ratio of 90 volumes of ethanol to 10 volumes of water. Lamina $h_3$ had a measured thickness of 1 mil and a measured $k\pi_3$ of 0.3 cm³·mil/cm²·hr. The laminated wall $h_T$ had a thickness of 4.5 mils, a $k\pi_T$ of 0.186 cm³·mil/cm²·hr, and an area of 2.27 cm². A passageway through $h_T$ had a diameter of 7 mils and the system had a rate of release of 30 mg per hr, with a variation of ±7% over a prolonged period of time.

EXAMPLE 6

The procedure of Example 5 is repeated but sodium chloride is replaced by nicotinamide, mannitol hexanitrate, isocarboxyazid, triamcinolone, tranylcyclopromine, meprobamate, nalamide, salicylamide, aspirin, theophylline, or theophylline monoethanolamine.

EXAMPLE 7

The physical and chemical integrity and the inertness of a laminated wall to drug was demonstrated as follows: first, a 10% polymeric solution of polyvinyl alcohol, 98% hydrolyzed grade, in a mixture of ethanol:water in the proportion of 20 parts of ethanol to 80 parts of water, by weight, was prepared by stirring the polymer and solvent in a high shear blender at 95° C for 15 minutes. Then, a lamina of the polymeric solution was cast with a Gardner knife onto a borosilicate substrate and dried at 40° C for 55 hours at atmospheric pressure. Finally, the lamina was crystallized in an oven at 170° C for 10 minutes. The lamina identified as $h_1$ had a thickness of 1.8 mils.

Next, a 10% lamina forming solution consisting of polymeric cellulose acetate having an acetyl content of 32% dissolved in dioxane was prepared by blending the polymer and the solvent in a high shear blender for 1 hr at 22.2° C and at atmospheric pressure. Then, a lamina $h_2$ of this lamina forming solution was cast with a Gardner knife directly onto the total, exposed surface of lamina $h_1$. Lamina $h_2$ had a thickness of 3.8 mils. Laminae $h_1$ and $h_2$ were dried in an oven for a week at 50° C to form a laminated wall that had a thickness $h_T$ of 5.6 mils.

Figure 7:
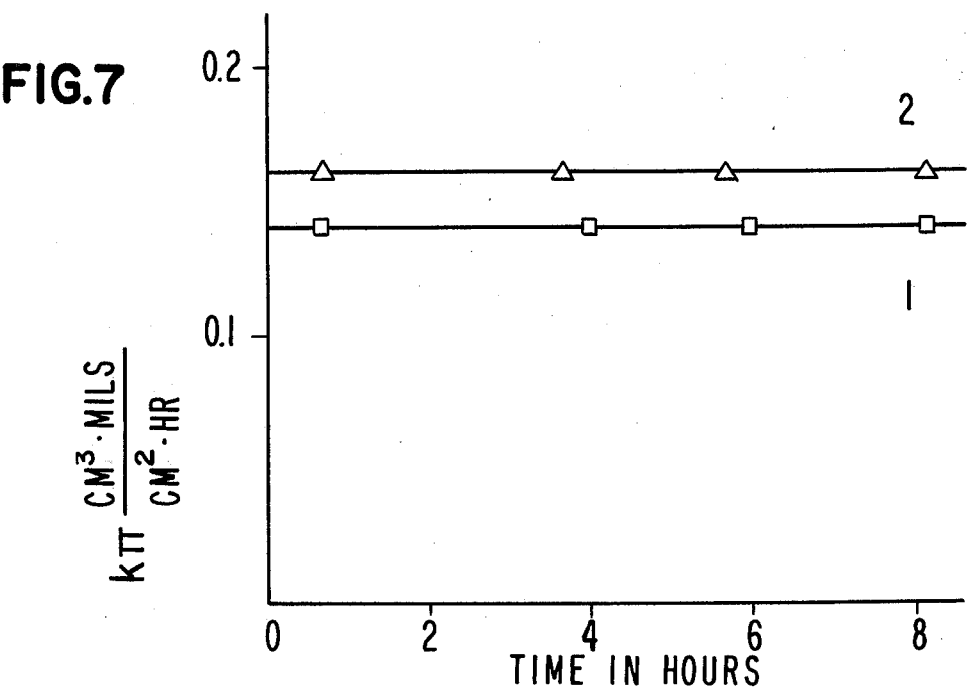
FIG. 7 is a graph illustrating the inertness of a laminated wall towards drug and the environment of use.

Then, the laminated wall was placed in an osmosis cell and its water transmission value $k\pi_T$ was measured using the drug sodium acetazolamide as an osmotic attractant. The laminated surface formed of crystallized semipermeable polyvinyl alcohol was placed in direct contact with the drug and the laminated surface of polymeric cellulose acetate was placed in contact with the environment consisting of water. The water transmission value for the laminated wall was measured for 6 hrs. and found to be 0.16 cm³·mil/cm²·hr. Then, a lamina $h_1$, consisting of crystallized polyvinyl alcohol as prepared above, was placed in the osmosis cell with one surface facing the drug and the other surface facing water, and its transmission value $k\pi_1$ measured for 8 hours. The transmission value found was 0.14 cm³·mil/cm²·hr. The measurements were made at periodic intervals and the results obtained were recorded in FIG. 7. In the figure, lamina $h_1$ is 1 and the laminated wall $h_2$, is 2. The results demonstrate the laminated wall maintains its physical and chemical integrity in the environment of use and towards the drug sodium acetazolamide. The results also show that lamina $h_1$ is nonerodible and inert to both the drug and the environment.

EXAMPLE 8

An osmotic therapeutic system for the controlled and continuous release of chlorpheniramine maleate is manufactured as follows: first, a 3% lamina forming solution of polymeric cellulose acetate having an acetyl content of 38.3% in acetone and a multiplicity of drug cores consisting of 300 mgs of sodium chloride and 1,000 micrograms of chlorpheniramine maleate are placed in a Wurster air suspension lamination machine and the cores air tumbled until a uniform lamina $h_1$ is applied to the drug core. The lamina has a thickness of 0.5 mil and a $k\pi_1$ of 0.054 cm³·mil/cm²·hr. Next, a second lamina, $h_2$, forming solution consisting of polymeric cellulose acetate having an acetyl content of 32% in acetone:water solvent consisting of 89:11, weight to weight, is added to the Wurster machine and lamina $h_1$ uniformly laminated with lamina $h_2$ to form the inert, laminated wall $h_t$. Lamina $h_2$ is 3 mils thick and had a $k\pi_2$ of 0.26 cm³·mils/cm²·hr. The laminated wall has a thickness of 3.5 mils and a $k\pi_T$ of 0.168 cm³·mils/cm²·hr. Finally, an aperature having a diameter of 7.5 mils is mechanically drilled through laminated wall $h_T$ to yield the osmotic therapeutic system. The laminated wall maintains its physical and chemical integrity in the presence of drug and in the environment of use. The system has a controlled and continuous rate of release of about 100 micrograms per hour chlorpheniramine maleate over a prolonged period of 10 hours.

EXAMPLE 9

The procedure of Example 8 is repeated with the lamination procedures as previously described, but the drug formulation of the example is replaced with a member selected from the group consisting of calcium gluconate, calcium lactate, potassium sulfate, potassium fluoride, sodium fluoride, ferrous lactate, ferrous gluconate, ferrous sulfate, ferrous fumurate and sodium lactate which drug is released in an effective amount at a controlled and continuous rate over a prolonged period of time.

The novel osmotic system of this invention use means for the obtainment of precise release rate in the environment of use while simultaneously maintaining the integrity and character of the system. While there has been described and pointed out features of the invention as applied to presently preferred embodiments, those skilled in the art will appreciate that various modifications, changes, additions and omissions in the systems illustrated and described can be made without departing from the spirit of the invention.

We claim:

1. An oral osmotic system sized and adapted for the controlled administration of drug to an animal, said system comprising:
   a. a shaped laminated wall comprising (1) a lamina formed of a material that maintains its physical and chemical integrity in the presence of fluid, drug and during the dispensing of drug, and is permeable to the passage of fluid and impermeable to the passage of drug, said lamina formed of a material having the general formula:

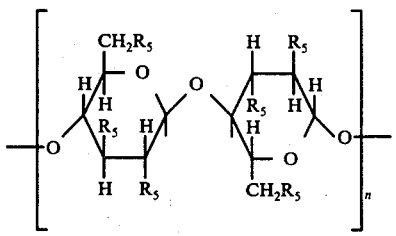

wherein $R_5$ is a member selected from the group consisting of hydroxyl, alkoxy, alkylcarbonate, alkylcarbamate, alkylsulfonate, alkylsulfamate and acyloxy, and wherein $n$ is a positive number greater than 5 and at least one R is acyloxy, said lamina laminated to (2) a lamina formed of a different material that maintains its physical and chemical integrity in the presence of fluid, drug and during the dispensing of drug, and is permeable to the passage of fluid and impermeable to the passage of drug, said lamina formed of the different material selected from the general formula:

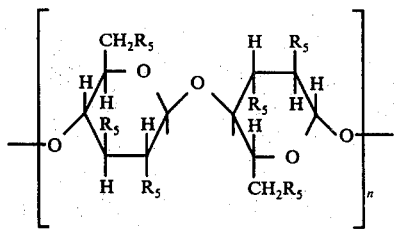

wherein $R_5$ is a member selected from the group consisting of hydroxyl, alkoxy, alkylcarbonate, alkylcarbamate, alkylsulfonate, alkylsulfamate, and acyloxy, and wherein $n$ is a positive number greater than 5 and at least one R is acyloxy; the wall surrounding and forming,
   b. a compartment containing a member selected from the group consisting of locally and systemically acting drugs;
   c. a passageway in the wall communicating with the compartment and the exterior of the system for administering drug from the system; and,
   d. wherein in operation when the system is in the animal fluid therefrom is imbibed through the laminated wall into the compartment in a tendency towards osmotic equilibrium at a rate determined by the permeability of the laminated wall and the osmotic pressure gradient across the laminated wall thereby continuously dissolving drug that is administered according to the following equation:

$$h_T/k\pi_T = h_1/k\pi_1 + h_2/k\pi_2$$

wherein $h_T$ is the thickness of the laminated wall, $h_1$ is the thickness of lamina (1,) $h_2$ is the thickness of lamina 2, $k\pi_T$ is the osmotic pressure of drug in the compartment times the permeability of the laminated wall to fluid, $k\pi_1$ is the osmotic pressure of drug in the compartment times the permeability of lamina (1) to fluid and $k\pi_2$ is the osmotic pressure of drug in the compartment times the permeability of lamina (2) to fluid, through the passageway at a controlled and continuous rate over a prolonged period of time.

2. The osmotic system for the controlled administration of drug according to claim 1, wherein the acyloxy in lamina (1) is a member selected from the group consisting of alkanoxyloxy, alkenyloxy and aroyloxy and the degree of substitution on each anhydroglucose unit is greater than from 0 up to 3.

3. The osmotic system for the controlled administration of drug according to claim 1, wherein the acyloxy in lamina (2) is a member selected from the group consisting of formyloxy, acetyloxy, propionyloxy, valeryloxy, heptanoyloxy, octanoyloxy, underanoyloxy, lauroyloxy, palmitoyloxy, steroyloxy, oleoyloxy, acryloxyloxy, methacryloyloxy, crotomyloxy, butenoyloxy, benzoyloxy, phenylacetyloxy, cinnamoyloxy, naphthoyloxy, ethoxybenzyloxy, and furoyloxy.

4. The osmotic system for the controlled administration of drug according to claim 1, wherein the material forming lamina (1) is a member selected from the group consisting of cellulose acetate acetoacetate dimethoxyethylcellulose acetate, cellulose acetate benzoate, cellulose acetate dimethylsulfamate, ethylcellulose dimethylsulfamate, cellulose acetate methylcarbonate, cellulose acetate ethylcarbonate, cellulose acetate methylcarbamate and cellulose acetate ethylcarbamate.

5. The osmotic system for the controlled administration of drug according to claim 1, wherein the material forming lamina (2) is a member selected from the group consisting of ethylmethylcellulose, hydroxyethylcellulose, hydroxypropylcellulose, hydroxyethyl methylcellulose, hydroxypropyl methylcellulose, ethylhydroxy ethylcellulose, and hexylpropyl cellulose.

6. The osmotic system for the controlled administration of drug according to claim 1, wherein the drug is present in the compartment mixed with an osmagent, and lamina (1) is formed of cellulose acetate having an acetyl content of 35 to 44.8%, and lamina (2) is formed of cellulose acetate having an acetyl content of 21 to 35%.

7. The osmotic system for the controlled administration of drug to an animal according to claim 1, wherein lamina (2) is formed of a member selected from the group consisting of cellulose triacetate, cellulose trivalerate, cellulose trilaurate, cellulose tripalmitate cellulose trisuccinate, cellulose triheptylate, cellulose tricaprylate, cellulose trioctanoate and cellulose tripropionate.

8. The osmotic system for the controlled administration of drug to an animal according to claim 1, wherein lamina (1) is formed of a member selected from the group consisting of cellulose disuccinate, cellulose dipalmitate, cellulose dioctanoate, cellulose dicaprylate and cellulose dipentanoate.

9. The osmotic system for the controlled administration of drug according to claim 1, wherein lamina (1) and lamina (2) exhibit a decreased permeability to the passage of fluid as the size is increased of the substituting group forming said laminae.

10. The osmotic system for the controlled administration of drug according to claim 1, wherein the compartment contains 0.05 ng to 5 grams of a drug that can be orally administered to produce a beneficial result.

11. The osmotic system for the controlled administration of drug according to claim 1, wherein lamina (1) is laminated to lamina (2) by successive air suspension lamination using an organic solvent selected from the group consisting of an alcohol, ketone, ester, ether, aliphatic hydrocarbon, halogenated hydrocarbon, cycloaliphatic aromatic, a heterocyclic, and solvent mixtures thereof.

* * * * *